US006599869B2

(12) United States Patent
Goo et al.

(10) Patent No.: US 6,599,869 B2
(45) Date of Patent: Jul. 29, 2003

(54) COMBINATION SOAP BAR COMPOSITION CONTAINING MONOGLYCERIDE SULFONATE AND ITS MANUFACTURING METHOD

(75) Inventors: Je-Kwon Goo, Daejeon (KR); Young-Ho Choi, Daejeon (KR); Moon-Jeong Rang, Daejeon (KR); Tae-Seong Kim, Daejeon (KR); Tae-Kyung Huh, Daejeon (KR); Jung-Jin Choi, Daejeon (KR); Ho-Jeong Ahn, Daejeon (KR)

(73) Assignee: LG Chemical Ltd, Seoul (KR)

( * ) Notice: Subject to any disclaimer, the term of this patent is extended or adjusted under 35 U.S.C. 154(b) by 0 days.

(21) Appl. No.: 10/114,412

(22) Filed: Apr. 2, 2002

(65) Prior Publication Data

US 2002/0142926 A1 Oct. 3, 2002

Related U.S. Application Data

(62) Division of application No. 09/454,105, filed on Dec. 3, 1999, now Pat. No. 6,413,922.

(30) Foreign Application Priority Data

Dec. 3, 1998 (KR) ........................................... 98-52775
Jul. 29, 1999 (KR) ........................................... 99-31025

(51) Int. Cl.[7] .................................................. A61K 7/50
(52) U.S. Cl. ....................... 510/156; 510/152; 510/153; 510/155; 510/458; 510/459; 510/492
(58) Field of Search ................................ 510/458, 459, 510/152, 141, 153, 155, 156, 492

(56) References Cited

U.S. PATENT DOCUMENTS

| | | | |
|---|---|---|---|
| 4,695,395 A | 9/1987 | Caswell et al. | 252/121 |
| 5,041,233 A | 8/1991 | Kutny et al. | 252/121 |
| 5,496,488 A | 3/1996 | Kacher et al. | 510/152 |
| 5,547,602 A | 8/1996 | Schuler | 510/152 |
| 5,683,683 A | 11/1997 | Scafidi | 424/70.19 |
| 6,008,173 A | 12/1999 | Chopra et al. | 510/152 |

*Primary Examiner*—Necholus Ogden
(74) *Attorney, Agent, or Firm*—Baker Botts L.L.P.

(57) ABSTRACT

The present invention relates to a combination soap bar composition containing monoglyceride sulfonates and a method for manufacturing the same. A combination bar composition containing monoglyceride sulfonates of the present invention comprises fatty acid based toilet bars and monoglyceride sulfonates of the following General Formula 1:

[General Formula 1]

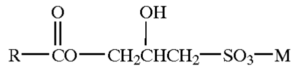

where R is an alkyl having 7 to 21 carbon atoms, and M is sodium, potassium, triethanolamine, or ammonium.

A combination bar composition containing monoglyceride sulfonates of the present invention has good general physical properties such as soap softness, etc. and very good moisturization properties and feel during usage even after repeated uses.

Furthermore, a combination liquid phase solution is manufactured by adding chloro sulfonates to a liquid phase soap which is produced from fatty acids, with the above combined liquid phase solution agitated, dried, and passed through soap manufacturing equipment in order to manufacture a combination soap bar containing monoglyceride sulfonates of the present invention. A method for manufacturing a combination bar containing monoglyceride sulfonates of the present invention involves a simple and economical manufacturing process. The quality of soap manufactured by the above method is equal to or higher than soap manufactured in a milling or slurry process after synthesizing monoglyceride.

5 Claims, No Drawings

COMBINATION SOAP BAR COMPOSITION CONTAINING MONOGLYCERIDE SULFONATE AND ITS MANUFACTURING METHOD

CROSS REFERENCE TO RELATED APPLICATION

This application is a divisional of U.S. patent application Ser. No. 09/454,105, filed Dec. 3, 1999 U.S. Pat. No. 6,413,922, which claims priority to Korean Patent Application Nos. 98-52775 and 99-31025, filed Dec. 3, 1998 and Jul. 29, 1999, respectively.

BACKGROUND OF THE INVENTION (a) Field of the Invention

The present invention relates to a combination soap bar composition containing monoglyceridesulfonate and its manufacturing method, more particularly to a combination soap bar composition containing monoglyceride sulfonate having superior moisturizing characteristics and feel during usage as well as a method for economically manufacturing a combination soap bar containing monoglyceride sulfonate.

(b) Description of the Related Art

Toilet soap bars which are made by saponifying fatty acids obtained by decomposing fats and fatty oils using calcium hydroxide, sodium hydroxide, etc. are generally used for washing human bodies. When toilet soap bars are used frequently, their sebum constituents of skin are excessively removed and the softened stratum corneum results in a possible cause of skin irritation since toilet soap bars are strongly alkaline. That is, when alkaline toilet soap bars are repeatedly used over a long time, the skin can become dried and loses its flexibility, easily causing problems of skin roughness. Various additives in toilet soap bar compositions which supply water and oil substances to the skin have been used in order to address the problems of skin drying and skin roughness attributable to the use of these alkaline toilet soap bars. There have also been attempts to alleviate skin drying by adding cosmetic materials, e.g., excess fatty agents, wetting agents, and plant extracts to soaps.

Moisturizing agents used in toilet soap bars, which put moisture on the surface layer of skin and act to block the moisture loss from the skin, play a role to reduce the moisture loss by forming a skin protection layer. Commonly applicable moisturizing agents for skin include glycerin, sorbitol, and natural oils. These form a skin protection layer by creating a membrane on the irregularities of a skin surface that has dried out due to the frequent use of alkaline soaps so that the moisture evaporation is restrained in order to alleviate further skin drying.

However, the current moisturizing agents do not have a function to adsorb external moisture for the skin, but only function in a role of acting as a temporary protective membrane. Furthermore, the current moisturizing agents do not have long lasting effects since they are easily broken away from the skin surface due to physical influences, and also have a problem in that the soap bars in which they are added are easily hydrated and softened when they are increasingly used by a bather in efforts to sustain their effects. That is, the current moisturizing agents do not influence the physiological functions of the skin due to their temporary effectiveness and in most cases actually unfavorably influence soap properties.

There has been increased interest in the manufacturing processes of soaps in which the surfactants are less irritating to the skin and have superior moisturizing effects than those contained in the general fatty acid based soaps in order to address these problems.

For example, a method for improving the moisturizing and feel during usage of liquid type body cleansers by mixing and using anionic, nonionic, and amphoteric surfactants is disclosed in U.S. Pat. No. 5,683,683. Although characteristics which each surfactant retain show synergy effect to constrain skin drying, and hence resulting in the moisturization of the skin when amphoteric surfactants are mixed and used with combination soap bars, an excessive amount of non inoic and amphoteric surfactants in these mixed surfactants has produced problems after long term storage with soap bar discoloration and reduce degrees of bubbling.

Furthermore, U.S. Pat. No. 4,695,395 discloses that the skin protection function is provided by having acyl isethionate, an anionic surfactant, in a combination bar. Although acyl isethionate is a low skin irritant and has superior usage due to its low liquidity and high hydrophilicity compared to general fatty acid based soaps, it has disadvantages in that its high solubility causes water to be easily absorbed into soap resulting in the deterioration of soap physical properties.

Furthermore, Korean Patent Publication No. 95-12209 mentions a method for manufacturing a combination soap bar containing active constituents in which acyl isethionate, a low skin irritant anionic surfactant, is contained as a supporting cleansing constituent. However, this method has not been very economical due to the complexity of its manufacturing method which comprises processes of manufacturing in advance acyl isethionate into certain specified dimensions using fatty acids and sodium isethionate, then processing the acyl isethionate into a slurry phase at a high temperature using liquid and solid phases, ionic water, etc., with the mixing of the slurry phase with a liquid phase soap.

SUMMARY OF THE INVENTION

It is an object of the present invention to provide a combination soap bar composition which has an improved soap softness, superior moisturizing effect and usage, and is a low skin irritant.

It is an other object of the present invention to provide a method for manufacturing a combination soap bar containing monoglyceride sulfonate in which the function of combination soap bar is maintained with a simple and economical manufacturing process, wherein a combination soap bar containing monoglyceride sulfonate having superior cleansing power and moisturizing characteristics and feel during usage is produced.

The present invention provides a fatty acid based toilet bar and a combination toilet soap bar composition containing 2 to 35 weight % of monoglyceride sulfonate of the following General Formula 1 in order to achieve the above objects:

[General Formula 1]

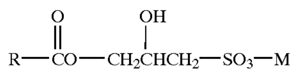

where R is an alkyl having 7 to 21 carbon atoms, and M is sodium, potassium, triethanolamine, or ammonium.

Furthermore, the present invention provides a method for manufacturing a combination soap bar containing monoglyceride sulfonate characterized in that the manufacturing processes consist of (a) manufacturing a fatty acid based liquid phase soap by adding electrolyte and neutralizer to fatty acids; (b) manufacturing mixed liquid phase soaps by adding chlorohydroxy sulfonate to the above liquid phase soaps and agitating; and (c) manufacturing soaps with the above associated soap manufacturing equipment by drying the above mixed liquid phase soaps.

DETAILED DESCRIPTION OF THE PREFERRED EMBODIMENTS

In the following detailed description, only the preferred embodiments of the invention have been shown and described, simply by way of illustration of the best mode contemplated by the inventor(s) of carrying out the invention. As will be realized, the invention is capable of modification in various obvious respects, all without departing from the invention. Accordingly, the description is to be regarded as illustrative in nature, and not restrictive.

The present invention is described in detail below.

The combination soap bar composition of the present invention contains general fatty acid based soaps as a main cleansing agent and 2 to 35 weight %, preferably 5 to 20 weight %, of monoglyceride sulfonate of the General Formula 1 below as a supporting cleansing agent.

Typical examples of monoglyceride sulfonate used in the present invention having the below General Formula 1 include sodium cocomoglyceride sulfonate, sodium tallow, monoglyceride sulfonate, sodium palm oil, monoglyceride sulfonate, sodium palm kernel monoglyceride sulfonate, etc. and a mixture made by mixing one or more of the above can be used:

[General Formula 1]

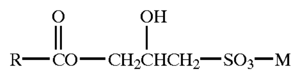

where R is an alkyl having 7 to 21 carbon atoms, and M is sodium, potassium, triethanolamine, or ammonium. RCOO having the above R is obtained from single or combined fatty acids which are derived from fats of tallow or lard, plant oil such as coconut oil, palm oil, or palm kernel oil.

Although monoglyceride sulfonate which manufactured by the following method is used in the present invention, its manufacture is not restricted to the following method.

Monoglyceride sulfonate can be manufactured after sodium chlorohydroxy sulfonate, an intermediate, is produced using epichlohydrin, reductant sodium sulfite, etc. The monoglyceride sulfonate used in the present invention is manufactured by transesterification using alkali salts of higher fatty acids. The above higher fatty acids can use a single or combined fatty acids which are derived from fats of tallow or lard, plant oil such as coconut oil, palm oil, or palm kernel oil.

The manufactured monoglyceride sulfonates show the following characteristics:

(i) low human skin irritation since it contains ester groups in its molecules;

(ii) even though it has a lower melting point than general fatty acid soaps, it has superior physical properties with water since it has a higher melting point and a lower solubility than other surfactants due to the affect of hydrogen bonds between the negative electric charges of hydroxy groups and sulfonates; and (iii) superior skin moisturization and feel during usage are provided due to the bond strength with water molecules enhanced by the hydroxy group of hydrophilic parts during the initial or repeated uses of soaps.

The soap softness is improved by the above characteristics and a combination soap bar composition having superior moisturization and feel during usage can be manufactured when 2 to 35 weight %, preferably 5 to 20 weight % of monoglyceride sulfonate, is used as a supporting cleansing agent in a combination soap bar composition of the present invention. When two or less weight % of the above combination soap bar composition is used, moisturization and 'feel during usage' characteristics deteriorate, even though the soap softness remains good. When 35 or more weight % of the above combination soap bar composition is used, softness of the toilet soap bar deteriorates, although moisturization and feel during usage remain superior Furthermore, general fatty acid based toilet soap bars can be used in the present invention that are made by neutralizing single or combined fatty acids obtained from animal oil and fat of beef tallow, lard, etc., plant oils such as coconut oil, palm kernel oil, palm oil, palm stearin oil, etc. with sodium hydroxide, potassium hydroxide, and triethanolamine. Typical examples of general fatty acid based toilet soap bars include sodium tallowyl soap, cocoyl soap, or a mixture of one or more thereof.

1 to 25 weight % of two to three or more surfactants salts normally used in a combination toilet soap bar, i.e., alkyl sulfates such as acyl isethionate, sodium laureth sulfate, sodium lauryl sulfate, etc., alkyl sulfosuccinate, alkyl glyceryl ether sulfonate, acyl sarcocinate, acyl taurate, alkyl sulfoacetate, and alkyl ether sulfate can be used considering the inherent characteristics of each surfactants in the range in which the effects of the present invention are not deteriorated in a combination soap bar composition of the present invention.

In order to manufacture the solid phase soaps with a combination soap bar composition of the present invention, a combination soap bar composition of the present invention can use a mixture of one or more compounds selected from the group consisting of binder, plasticizer, and vehicle. Binder and plasticizer improve the soap manufacturing workability by providing soaps with bond strength and plasticity. They also influence the soap hardness after manufacturing and physical properties such as softness, degree of bubbling, smoothness, etc. while in use. Higher fatty acids such as those generally used higher fatty alcohols, coconut fatty acids, etc., hardened oil and fat, paraffin wax, polyester, polyethylene glycol, sodium stearate, hardened cator oil, fatty alkyl ketone, etc. can also be used. Furthermore, ordinarily used dextrin, starch, salt, talc, etc. can be used as vehicle, which plays a role of maintaining the interior structural stability of the final products or the product harness Furthermore, 5 to 20 weight % of moisture, and other constituents used in a normal toilet soap bar, that is pigments like white pigment such as titanium dioxide, etc., perfumes, antioxidant, metallic ion sealing agents such as ethylenediaminetetraacetic acid, etc., and other additives can be used in a combination soap bar composition according to the present invention. The other constituents, however, except for moisture, are used in very small amounts.

A combination soap bar explained in the present invention can be manufactured by various methods. Manufacturing methods of ordinary combination soap bars include a manufacturing method consisting of the steps of adding cleansing agent and additives to a mixer and then mixing in a mixture for a certain period, remixing the mixture uniformly in the milling process, and consequently manufacturing soap in a general soap process. Additionally there is another manufacturing method consisting of the steps of manufacturing part or all of the additives except for the main cleansing agent in a slurry, mixing the slurry with main cleansing agent, and consequently manufacturing soap in a general soap process.

Although a method for manufacturing a combination soap bar composition for an embodiment of the present invention comprises the steps of adding monoglyceride sulfonate and other additives to a mixture of fatty acid based toilet soap bar, mixing for five minutes, and then uniformly mixing the mixture in a three stage roll mill, and then mixing, molding, extruding and forming a shape according to an ordinary soap manufacturing process, the combination soap bar manufacturing method of the present invention is not restricted to this.

Furthermore, the present inventors found that a combination soap bar composition having superior general physical properties and moisturization could be manufactured by manufacturing a low irritant anionic surfactant and monoglyceride sulfonate as a supporting cleansing agent of general fatty acid based soaps, roll milling or making monoglyceride sulfonate into a slurry phase and containing it in a soap. However, the above soap manufacturing method is not economical since after a supporting cleansing constituent of monoglyceride sulfonate is manufactured, soap is manufactured by reprocessing it with a milling or a slurry process of a general fatty acid based soap.

Therefore, as a result of continuous studies on how to manufacture a combination soap bar containing a supported cleansing agent, i.e., monoglyceride sulfonate, in an economical way, the present inventors generated a manufacturing method of a combination soap bar containing monoglyceride sulfonate of the present invention by discovering that when chlorohydroxy sulfonate (hereinafter referred to as "chlorosulfonate") is added to a liquid phase soap in a soap manufacturing process and certain reaction conditions are provided, a combination soap bar containing monoglyceride sulfonate can be manufactured, and the quality of the physical properties and mosturization of the soap can be maintained at the same or at a higher level during water absorption, when compared to a soap manufactured in a milling or a slurry phase after synthesizing monoglyceride sulfonate.

The present invention is a method for manufacturing a combination soap bar containing monoglyceride sulfonate characterized in that the soap manufacturing processes in soap manufacturing equipment consist of (a) manufacturing fatty acid based liquid phase soap by adding electrolyte and neutralizer to fatty acids; (b) manufacturing a mixed liquid phase soap by adding chlorohydroxy sulfonate to the above liquid phase soap and agitating; and (c) drying the above mixed liquid phase soap.

The above fatty acid based liquid phase soap of the present invention is manufactured by adding electrolyte and neutralizer to fatty acids, and the moisture content is preferably 20 to 35 weight %. The above fatty acids are single or combined fatty acids obtained from animal oil and fat such as beef tallow, lard, etc., plant oil such as coconut oil, palm kernel oil, palm oil fat, palm stearin oil, etc.

Alkali metal, more preferably sodium chloride, is used as the above electrolyte. The above sodium chloride is preferably 0.01 to 1 weight %, more preferably 0.1 to 0.5 weight % of fatty acid based liquid phase soap. Furthermore, the above neutralizer is 25 to 50% (w/w) of sodium hydroxide or potassium hydroxide solution.

Furthermore, fatty acids, electrolytes and neutralizers to be used in the above liquid phase soap manufacturing are reacted in a temperature range of 50 to 90 degrees centigrade, preferably 60 to 80 degrees centigrade, and a liquid phase soap formed by the above reaction should be maintained in a temperature range of 75 to 100 degrees centigrade, preferably 85 to 95 degrees centigrade. A liquid phase soap temperature should be maintained by adjusting an increasing temperature of these additives since temperature generally increases due to an exothermic reaction when neutralizers are added to fatty acids.

Furthermore, the above chlorosulfonates are preferably 1 to 12 weight %, more preferably 2 to 7 weight %, of a combination liquid phase bar manufactured by mixing the above fatty acid based liquid phase soap with chlorosulfonates. The monoglyceride amount is also less in a manufactured combination soap bar when the above chlorosulfonate amount is less than 1 weight %. The viscosity or phase of a combination liquid phase soap is also changed so that the smooth manufacturing of soaps in the ordinary fatty acid based soap manufacturing equipment can be difficult when chlorosulfonates exceed 12 weight %.

One example of the methods for manufacturing the above chlorosulfonates to be used in the present invention is as follows. After a reductant, sodium sulfite, sodium bisulfite, or sodium methabisulfite, is mixed and dissolved with water, epichlohydrine is added and chloro sulfates are manufactured by reaction. The structural formula of chlorosulfonate manufactured by the above method is as in General Formula 2:

[General Formula 2]

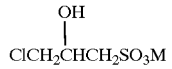

where M is sodium, potassium, ammonium or triethanol ammonium.

There is also a method (hereinafter referred to as "continuous type process") for mixing with a liquid phase soap by manufacturing chlorosulfonate solution and another method (hereinafter referred to as "batch type process") for putting a powder phase chlorosulfonate into a liquid phase soap among the methods for adding chlorosulfonates in the present invention. The continuous type process is preferable.

The chlorosulfonate solution to be used in the above continuous type process is manufactured by dissolving chlorosulfonate with water, with the above solution containing 20 or more weight %, preferably 30 to 45 weight %, of chlorosulfonates and manufactured at a temperature of 20 or more degrees centigrade, preferably 40 to 70 degrees centigrade. Although a chlorosulfonate solution without water can be used by mixing polyhydric alcohols (such as propylene glycol, glycerin, sorbitol, polyoxyethylene glycol), oils (such as mineral oil), and neutralizers (such as caustic soda, caustic potash, and triethanolamine), it is preferably manufactured such that chlorosulfonates are not in a supersaturation condition, if possible.

A batch type manufacturing method, a method wherein monoglycerides are contained in a combination soap bar by putting a certain amount of powder type chlorosulfonate into a liquid phase soap of which the weight and volume are known, is the same manufacturing process as a continuous type process except that chlorosulfonates are added in a powder phase and not in a solution phase. A powder phase chlorosulfonate used in a batch type process is composed of 90 or more weight %, preferably 95 or more weight %, of active constituents.

The temperature of liquid phase soaps and chlorosulfonate solution is properly maintained and increased such that the temperature of a combination liquid phase soap is maintained from 75 to 100 degrees centigrade, preferably 85 to 95 degrees centigrade, in the manufacturing process of a combination soap bar composition of the present invention.

Even if particular mentions are not made herein, a batch type process is to be regard as having equal status with a continuous type process in the manufacturing process of a combination soap bar composition of the present invention. Proper managing of temperature, agitating speed, and time of the combination the liquid phase soap with manufacturing methods and conditions of fatty acid based liquid phase soap and chlorosulfonate solution is necessary in order to maximize the yield of monoglyceride sulfonates by adding chlorosulfonates to a liquid phase soap. Monoglyceride sulfonate formed during the above agitating procedure can be represented in the following General Formula 1:

[General Formula 1]

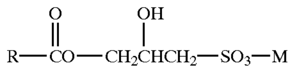

where R is an alkyl having 7 to 21 carbon atoms, and M is sodium, potassium, ammonium, or triethanolammonium.

Although the above agitating speed depends on the volume of the reactor in which a combination liquid phase soap is contained, there is not much difference in the contained formation amount in the present invention so long as there is an agitating speed such that a combination liquid phase soap has the sufficient contact area. If possible, a high speed agitation is preferable.

Furthermore, a constant agitating time, temperature, and agitating speed are necessary in order to form monoglyceride sulfonates in a combination liquid phase soap. A combination liquid phase soap is agitated for more than 20 minutes, preferably 30 minutes to 4 hours, since added chlorosulfonates can exist in a non-reacted condition not participating in the reaction, and the formed monoglyceride sulfonates are hydrolyzed to influence on the yield.

Although a part of chlorosulfonate used in the present invention and formed monoglyceride sulfonate is hydrolyzed in an alkali and at a high temperature to form a part of dihydroxypropane sulfonate and sodium chloride as a side reactant, it is not at a level so as to influence quality. A solid phase soap falling within manufacturing and commercial parameters when chlorosulfonates are used is within the range of the present invention.

Furthermore, additives which can normally be used in a toilet soap bar, i.e., perfumes, pigment, antioxidant, metallic ion sealing agent, etc., can be added during the manufacturing process of a combination soap bar or after the manufacturing of a cleansing agent in a combination soap bar composition of the present invention.

When soap is manufactured in soap manufacturing equipment by drying a combination liquid phase soap of the present invention, a combination soap bar containing monoglyceride sulfonates is produced. All generally usable drying methods and soap manufacturing equipment can be used in the above drying method and soap manufacturing process.

Examples and comparative examples of the present invention are described below. However, the following examples are only for illustrating the present invention and the present invention is not restricted to the following examples.

EXAMPLE 1

After uniformly mixing a composition comprising 76.65 weight % of sodium tallow oil/coco-oil soap, 6.0 weight % of sodium coco monoglyceride sulfonate, 3.0 weight % of coconut oil fatty acid, 1.0 weight % of salt, 12.0 weight % of moisture, 0.05 weight % of ethylenediaminetetra acid, 0.3 weight % of titanium dioxide, and 1.0 weight % of perfumes in an amalgamator and 3 stage roll mill, soap was manufactured by shaping through molding and extrusion processes in general fatty acid based toilet soap bar manufacturing equipment.

EXAMPLES 2 TO 3

Soap was manufactured by the same method as in the above Example 1 except that the amount of each constituents was changed as represented in the following Table 1.

COMPARATIVE EXAMPLES 1 TO 7

Soap was manufactured by using constituents represented in the following Table 1 in ratios as represented in the following Table 1 and by the same method as in the above Example 1.

TABLE 1

(Unit: weight %)

| | Exam 1 | Exam 2 | Exam 3 | Com Exam 1 | Com Exam 2 | Com Exam 3 | Com Exam 4 | Com Exam 5 | Com Exam 6 | Com Exam 7 |
|---|---|---|---|---|---|---|---|---|---|---|
| Sodium tallowyl/cocoyl soap | 76.65 | 70.65 | 64.65 | 86.65 | 82.65 | 82.65 | 76.65 | 64.65 | 79.65 | 73.65 |
| Sodium coco monoglyceride sulfonate | 6.0 | 12.0 | 18.0 | 0 | 0 | 0 | 0 | 0 | 0 | 0 |
| Sodium cocoyl lisethionate | 0 | 0 | 0 | 0 | 0 | 0 | 6.0 | 18.0 | 0 | 0 |
| Sodium laureth sulfate | 0 | 0 | 0 | 0 | 0 | 0 | 0 | 0 | 6.0 | 12.0 |
| Cocoyl fatty acid | 3.0 | 3.0 | 3.0 | 0 | 3.0 | 0 | 3.0 | 3.0 | 0 | 0 |
| Glycerin | 0 | 0 | 0 | 0 | 0 | 3.0 | 0 | 0 | 0 | 0 |
| Salt | 1.0 | 1.0 | 1.0 | 1.0 | 1.0 | 1.0 | 1.0 | 1.0 | 1.0 | 1.0 |
| Moisture | 12.0 | 12.0 | 12.0 | 12.0 | 12.0 | 12.0 | 12.0 | 12.0 | 12.0 | 12.0 |
| Ethylene-diaminetetraacetic acid | 0.05 | 0.05 | 0.05 | 0.05 | 0.05 | 0.05 | 0.05 | 0.05 | 0.05 | 0.05 |
| Titanium dioxide | 0.3 | 0.3 | 0.3 | 0.3 | 0.3 | 0.3 | 0.3 | 0.3 | 0.3 | 0.3 |
| Perfumes | 1.0 | 1.0 | 1.0 | 1.0 | 1.0 | 1.0 | 1.0 | 1.0 | 1.0 | 1.0 |

EXAMPLES 4 to 7

Soap was manufactured by the same method as the above Example 1 using constituents represented in the following Table 2 in amounts as represented in the following Table 2.

COMPARATIVE EXAMPLES 8 to 11

Soap was manufactured by the same method as the above Example 1 using constituents represented in the following Table 2 in amounts as represented in the following Table 2.

TABLE 2

(Unit: weight %)

| | Exam 4 | Exam 5 | Exam 6 | Exam 7 | Com Exam 8 | Com Exam 9 | Com Exam 10 | Com Exam 11 |
|---|---|---|---|---|---|---|---|---|
| Sodium tallowyl/cocoyl soap | 81.65 | 48.65 | 77.65 | 75.65 | 83.65 | 44.65 | 79.65 | 79.65 |
| Sodium coco monoglyceride sulfonate | 3.0 | 32.0 | 0 | 0 | 1.0 | 38.0 | 0 | 0 |
| Sodium tallowyl/cocoyl monoglyceride sulfonate | 0 | 0 | 6.0 | 6.0 | 0 | 0 | 0 | 0 |
| Sodium laureth sulfate | 0 | 0 | 0 | 2.0 | 0 | 0 | 0 | 0 |
| Cocoyl fatty acid | 1.0 | 5.0 | 2.0 | 2.0 | 1.0 | 3.0 | 0 | 6.0 |
| Sorbitol | 0 | 0 | 0 | 0 | 0 | 0 | 6.0 | 0 |
| Salt | 1.0 | 1.0 | 1.0 | 1.0 | 1.0 | 1.0 | 1.0 | 1.0 |
| Moisture | 12.0 | 12.0 | 12.0 | 12.0 | 12.0 | 12.0 | 12.0 | 12.0 |
| Ethylene-diamine-tetraacetic acid | 0.05 | 0.05 | 0.05 | 0.05 | 0.05 | 0.05 | 0.05 | 0.05 |
| Titanium dioxide | 0.3 | 0.3 | 0.3 | 0.3 | 0.3 | 0.3 | 0.3 | 0.3 |
| Perfumes | 1.0 | 1.0 | 1.0 | 1.0 | 1.0 | 1.0 | 1.0 | 1.0 |

Softness, moisturization, and feel during usage for a combination soap bar manufactured according to methods of the above Examples 1 to 7 and Comparative Examples 1 to 11 were measured according to the following test methods Additionally soap softness was measured by comparing water absorption and soap bar appearance after water absorption.

Test 1

Water Absorption

After sticking soap of weight ($W_1$) with a weighed pin ($W_2$) and immersing it into a thermo water vat at 25 degrees centigrade for 4 hours, it was taken out, dried for one hour at a soap drying device at 20 to 25 degrees centigrade and weighed ($W_3$). Consequently, the measured results of water absorption according to the following Equation 1 were represented in the following Table 3:

$$\text{Water absorption }(\%)=\{[(W_2+W_3)-(W_1+W_2)]/W_1\}\times 100. \quad \text{[Equation 1]}$$

The greater the degree of water absorption means the worse physical properties are, since the capability to contain water becomes bigger. Additionally, the degree of water absorption of a general fatty acid based toilet soap bar is normally from 5 to 25%.

Test 2

Appearance After Water Absorption

After immersing a soap bar at 25 degrees centigrade for 4 hours during a water absorption test of the above Test 1, it was taken out, and the soap's appearance and surface conditions were evaluated with the following standards.

Evaluation Standard

○: soap is not swollen and its appearance is clean

Δ: soap is a little swollen and some protrusions and depression patterns, etc. are formed on the surface,X : soap is severely swollen and the water absorbed areas have lost their solid shape and exhibit flowing.

Test 3

Moisturizing Test

After soap manufactured according to Examples 1 to 7 and Comparative Examples 1 to 11 was diluted with distilled water to make a 4% aqueous solution, 0.5 ml of this aqueous solution was taken and rubbed on an 5 cm×5 cm area inside a test subject's arm for one minute, allowed to remain on the arm for 30 seconds, and then washed with the running water for 10 seconds. The moisture retaining amount was twice measured 30 minutes after washing (first time/second time) over a 3 hour interval per day. This data was compared with the moisture retaining amount before washing by employing the below Equation 2:

$$\text{Moisture retaining amount }(\%)=\{(\text{retaining amount before washing}-\text{retaining amount after washing})/\text{retaining amount before washing}\}\times 100. \quad \text{[Equation 2]}$$

The instrument used for this test was a Skicon 200 device and the test was performed with a thermohydrostat at a temperature of 25 degrees centigrade and relative humidity of 50%.

Test 4

Usage Test

Fifteen (15) men and women were selected to respectively use soap compositions manufactured according to Examples 1 to 7 and Comparative Examples 1 to 11. The soap compositions were used with tap water in a general method for using a toilet soap bar, and marks were given on the basis of the categories of the following Table 3, and the average values of these marks are represented below.

TABLE 3

| | Feel During Usage |
|---|---|
| 5 points | Smoothness and the touch of the bar are very good |
| 4 points | Smoothness and the touch of the bar are somewhat good |
| 3 points | Smoothness and degree of bubbling are average |
| 2 points | Smoothness and the touch of the bar are somewhat bad |
| 1 point | Smoothness and the touch of the bar are very bad |

The 'Feel During Usage' value for an ordinary fatty acid based toilet bar is over 3.0.

After measuring water absorption, appearance after absorption, feel during usage and moisturization (first and second) with the above methods, the measured results were represented in the following Tables 4 and 5.

TABLE 4

| | Water absorption [%] | Appearance after water absorption | Feel During Usage | Moisturization (first) [%] | Moisturization (second) [%] |
|---|---|---|---|---|---|
| Example 1 | 16.2 | ○ | 4.0 | 59.3 | 54.2 |
| Example 2 | 18.3 | ○ | 4.3 | 63.8 | 59.8 |
| Example 3 | 20.6 | ○ | 4.5 | 71.5 | 67.3 |
| Comparative Example 1 | 18.5 | ○ | 3.1 | 41.2 | 33.5 |
| Comparative Example 2 | 17.3 | ○ | 3.5 | 44.5 | 38.4 |
| Comparative Example 3 | 29.5 | Δ | 3.8 | 51.3 | 43.5 |
| Comparative Example 4 | 21.4 | ○ | 4.0 | 52.5 | 45.6 |
| Comparative Example 5 | 32.3 | X | 4.1 | 60.7 | 54.0 |
| Comparative Example 6 | 31.3 | X | — | — | — |
| Comparative Example 7 | 43.5 | X | — | — | — |

TABLE 5

| | Water absorption [%] | Appearance after water absorption | Feel During Usage | Moisturization [%] (first) [%] | Moisturization [%] (second) [%] |
|---|---|---|---|---|---|
| Example 4 | 14.8 | ○ | 3.6 | 54.1 | 49.3 |
| Example 5 | 23.1 | ○ | 4.1 | 74.5 | 71.6 |
| Example 6 | 16.3 | ○ | 3.9 | 58.3 | 53.0 |
| Example 7 | 21.8 | ○ | 4.0 | 59.5 | 54.1 |
| Comparative Example 8 | 17.5 | ○ | 3.3 | 47.1 | 40.7 |
| Comparative Example 9 | 29.5 | Δ | 4.2 | 75.0 | 73.1 |
| Comparative Example 10 | 34.3 | X | — | — | — |
| Comparative Example 11 | 15.2 | ○ | 3.7 | 48.5 | 43.5 |

It can be seen as represented in the above Table 4 and Table 5 that when monoglyceride sulfonates are used as a supporting cleansing agent in an ordinary fatty acid based soap within the range of the present invention or mixed with other surfactants, a combination soap bar composition of the present invention is superior to an ordinary fatty acid based soap and/or the same soap containing moisturizer, etc. in terms of initial moisturization, moisturization following repeated uses. Additionally, the usage quality, physical properties, and appearance quality after water absorption are maintained in a similar manner as does an ordinary fatty acid based soap.

It can also be shown that a combination soap bar composition of the present invention is superior to a soap containing acyl isethionate or alkyl sulfates, surfactants which are generally used in a combination soap bar, in terms of physical properties during water absorption, and is good at moisturization during both initial and repeated use.

However, it can be shown that when the amount of monoglyceride sulfonates used is low, moisturizing effects and quality improving effects of the feel during usage is reduced while general physical properties remain good. Additionally, when the amount of monoglyceride sulfonates used exceeds a certain amount, physical properties during water absorption and appearance after water absorption are bad while moisturizing effects remain superior.

Manufacturing of Chlorosulfonate Solution

EXAMPLE 8

After putting 70 weight parts of purified water into a reactor and increasing the temperature to 35 degrees centigrade, a chlorosulfonate solution was manufactured by adding 30 weight parts of chlorosulfonate.

EXAMPLE 9

After putting 60 weight parts of purified water into a reactor and increasing the temperature to 60 degrees centigrade, a chlorosulfonate solution was manufactured by adding 40 weight parts of chlorosulfonate.

EXAMPLES 10 TO 11

Chlorosulfonate solutions of Examples 10 to 11 were manufactured with the same constituents and at the same temperature as indicated in Table 6 with the same method as described in Example 8 except that glycerin and potassium hydroxide were put into the reactor before adding chlorosulfonates.

TABLE 6

| Classification | Formulations (weight parts) | | | | Manufacturing temperature Degrees |
|---|---|---|---|---|---|
| Raw materials | Purified water | Chloro-sulfonate | Glycerin | Potassium hydroxide | centigrade (° C.) |
| Example 8 | 70 | 30 | — | — | 35 |
| Example 9 | 60 | 40 | — | — | 60 |
| Example 10 | 60 | 35 | 5 | — | 70 |
| Example 11 | 52 | 45 | — | 3 | 70 |

Manufacturing of a Combination Bar Containing Monoglyceride Sulfonate

EXAMPLE 12

After mixing beef tallow and coconut fatty acid in a ratio of 80:20 (w/w) and adding 0.25 weight parts of sodium chloride to a mixture, 100 weight parts of liquid phase soap at 95 degrees centigrade was manufactured using a sodium hydroxide aqueous solution in order to produce a liquid phase soap with 30 weight parts moisture content. After manufacturing a chlorosulfonate solution in which 40 weight parts of chlorosulfonate was contained in purified water at 60 degrees centigrade in a separate mixer, 100 weight parts of a combination liquid phase soap at 90 degrees centigrade were manufactured in a continuous mixer by adding in appropriate amounts to achieve 90 weight parts of liquid phase soap and 10 weight parts of chlorosulfonate solution. After reacting the above combination liquid phase soap in a Homo Mixer at 100 revolutions per minute for 180 minutes and then drying it, a cleansing agent containing 13 weight % of moisture was manufactured. A combination soap bar was manufactured through molding, extrusion, and formation processes in ordinary fatty acid based soap manufacturing equipment by adding 1.2 weight parts perfumes and 0.3 weight parts titanium dioxide to 100 weight parts of the above cleansing agent.

EXAMPLES 13 TO 15

A combination bar containing monoglyceride sulfonates was manufactured in Examples 13 to 15 in the same method as used for Example 12 except that it was manufactured with the constituents and conditions as specified in Table 7.

TABLE 7

| Classification | Composition or manufacturing conditions | Example 12 | Example 13 | Example 14 | Example 15 |
|---|---|---|---|---|---|
| Cleansing agent composition (weight parts) | Sodium tallow oil/coco-oil soap solution | 90.0 | 96.0 | 92.3 | 85.0 |
| | Chlorosulfonate solution | 10.0 | 4.0 | 7.7 | 15.0 |
| Additives (weight parts) | Perfumes | 1.2 | 1.2 | 1.2 | 1.2 |
| | Titanium dioxide | 0.3 | 0.3 | 0.3 | 0.3 |
| Reaction conditions | Temperature of a combination liquid phase soap (° C.) | 95 | 92 | 88 | 85 |
| | Agitating speed (revolutions per minute) | 100 | 600 | 1,200 | 30 |
| | Agitating time (minute) | 180 | 120 | 60 | 240 |
| Yield | Formation ratio per theoretical value (%) | 71.5 | 74.4 | 82.6 | 70.1 |

EXAMPLE 17

Soap was manufactured in the same compositions and manufacturing conditions as represented in Table 8 and with the same method as in Example 16.

COMPARATIVE EXAMPLE 12

After uniformly mixing a composition comprising 77.0 weight parts of sodium tallowyl/cocoyl soap, 6.0 weight parts of sodium tallowyl/cocoyl monoglyceride sulfonate, 1.5 weight parts of tallow/coco fatty acid, 1.0 weight part of sodium chloride, 13.0 weight parts of moisture, 0.3 weight parts of titanium dioxide, and 1.2 weight parts of perfumes with amalgamator in a 3 stage roll mill, soap was manufactured through the molding, extrusion, and formation processes of ordinary fatty acid based toilet soap bar manufacturing equipment.

COMPARATIVE EXAMPLE 13

Soap was manufactured in the same method as with Comparative Example 12 except that compositions were the same as represented in Table 8.

TABLE 8

| Classification | Compositions or manufacturing conditions | Example 16 | Example 17 | Comparative Example 12 | Comparative Example 13 |
|---|---|---|---|---|---|
| Cleansing agent compositions (weight parts) | Sodium tallowyl/cocoyl soap solution (25 to 35 weight % of moisture contained) | 90.0 | 95.0 | — | — |
| | Chlorosulfonates | 10.0 | 5.0 | — | — |
| | Sodium tallowyl/cocoyl soap | — | — | 77.0 | 72.0 |
| | Sodium tallowyl/cocoyl monoglyceride sulfonates | — | — | 6.0 | 10.0 |
| | Tallow/coco fatty acid | — | — | 1.5 | 2.0 |
| Additives (weight parts) | Perfumes | 1.2 | 1.2 | 1.2 | 1.2 |
| | Titanium dioxide | 0.3 | 0.3 | 0.3 | 0.3 |
| | Sodium chloride | — | — | 1.0 | 1.5 |
| | Moisture | — | — | 13.0 | 13.0 |
| Agitating conditions | Temperature of a combination liquid phase soap (° C.) | 92 | 94 | — | — |
| | Agitating speed | 600 | 50 | — | — |
| | Agitating time | 60 | 120 | — | — |
| Yield | Formation amount per theoretical value (%) | 78.5 | 74.5 | — | — |

EXAMPLE 16

After mixing beef tallow and coconut fatty acid in a ratio of 60:40 (w/w) and adding 0.10 weight parts of sodium chloride, 100 weight parts of liquid phase soap at 92 degrees centigrade was manufactured using a sodium hydroxide solution in order to achieve a liquid phase soap with 33 weight parts moisture content. After adding 90 weight parts of the above liquid phase soap to a mixer, 100 weight parts of a combination liquid phase soap at 92 degrees centigrade was manufactured by adding 10.0 weight parts powder chlorosulfonate to a mixer. After reacting the above combination liquid phase soap in a mixer at 600 revolutions per minute for about 60 minutes and then drying it, a cleansing agent containing moisture content of 13 weight % was manufactured. Combination soap was manufactured in ordinary fatty acid based soap manufacturing equipment through molding, extrusion, and formation processes by adding 1.2 weight parts perfumes and 0.3 weight parts titanium dioxide to 100 weight parts of the above cleansing agent.

Test 5

Water Absorption Test

After sticking a combination soap bar of a particular weight ($W_1$) containing monoglyceride sulfonate manufactured in the above Examples 12 to 17 and Comparative Examples 12 to 13 with a weighed pin ($W_2$) and immersing it into a thermo water vat at 25 degrees centigrade for 4 hours, it was taken out, dried for one hour in a soap drying device at 20 to 25 degrees centigrade and then weighed ($W_3$). Consequently, the measured results of water absorption were reduced according to the following Equation 3 and were represented in the following Table 9:

$$\text{Water absorption } (\%)=\{[(W_2+W_3)-(W_1+W_2)]/W_1\}\times 100. \quad \text{[Equation 3]}$$

The greater the degree of water absorption means the worse physical properties are, since the capability to contain water becomes bigger. Additionally the degree of water absorption of a general fatty acid based toilet bar is normally from 5 to 25%.

Test 6 Appearance After Water Absorption

After immersing soap samples of Examples 12 to 17 and Comparative Examples 12 to 13 at 25 degrees centigrade for 4 hours during a water absorption test of the above Test 5, it was taken out, and the soap's appearance and surface conditions were evaluated using the following standards.

Evaluation Standard good: soap is not swollen and its appearance is clean fair: soap is a little swollen and some protrusions, and depression patterns, etc. are formed on the surface, bad: soap is severely swollen out and the absorbed areas have lost their solid shape and exhibit flowing.

Test 7

Moisturization Test

After soap samples manufactured according to Examples 12 to 17 and Comparative Examples 12 to 13 were diluted with distilled water to make 4% aqueous solution, 0.5 ml of this aqueous solution was taken and rubbed on a 5 cm×5 cm area inside an arm of a test subject for one minute, allowed to remain on the arm for 30 seconds, and then washed with the running water for 10 seconds. The moisture retaining amount was measured on for each soap sample 30 minutes after washing and these measurements were reduced according to the below Equation 4, with the results represented in Table 9:

Moisture retaining amount (%)=[(retaining amount before washing−retaining amount after washing)/retaining amount before washing]×100. [Equation 4]

The instrument used in the present test was a Skicon 200 device and the test was performed with a thermohydrostat at a temperature of 25 degrees centigrade and relative humidity of 50%. The moisture retaining value of an ordinary fatty acid based soap is generally between 45 to 55.

TABLE 9

| Classification | Degree of water absorption (%) | Appearance during inspection | Moisturization (%) |
|---|---|---|---|
| Example 12 | 15.2 | Good | 65.1 |
| Example 13 | 18.0 | Good | 55.1 |
| Example 14 | 20.5 | Good | 60.5 |
| Example 15 | 16.5 | Good | 68.6 |
| Example 16 | 20.2 | Good | 70.5 |
| Example 17 | 17.6 | Good | 64.1 |
| Comparative Example 12 | 18.5 | Good | 60.5 |
| Comparative Example 13 | 16.5 | Good | 68.6 |

As shown in the above Table 9, soaps of Examples 12 to 17 have 15.2 to 20.5% of water absorption which is similar to 16.5 to 18.5% of Comparative Examples 12 to 13, good appearance inspection results when compared with Comparative Examples 12 to 13, and 55.1 to 70.5% moisturization, which is similar to the 60.5 to 68.6% moisturization of Comparative Examples 12 to 13. Particularly, the moisturization of Example 16 was very good as it had a value of 70.5%. Therefore, the above results represent that the quality of soaps manufactured according to Examples 12 to 17 have similar levels of quality as do the soaps manufactured according to Comparative Examples 12 to 13.

On the other hand, soaps containing monoglyceride sulfonates of the above Examples 12 to 17 and Comparative Examples 12 to 13 have superior moisturization values when compared to the 45 to 55% values of ordinary fatty acid based soaps represented in Table 9.

As described above, a combination bar composition of the present invention has good general physical properties such as soap softness, etc. and very good moisturization properties and feel during usage even following repeated uses.

As reviewed above, a manufacturing method of soaps containing monoglyceride sulfonates of the present invention is simple and economical, and a soap containing monoglyceride sulfonates produced by the present invention is equal to or higher in quality when compared to a soap which is manufactured in multi stage method, i.e., a method where monoglyceride sulfonates are first manufactured and mixed with a liquid phase soap solution prior to manufacturing a final soap.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for manufacturing a combination soap bar containing monoglyceride sulfonates wherein said method comprises:

(a) adding electrolyte and neutralizer to fatty acids to produce a fatty acid based liquid phase soap;

(b) adding chlorohydroxy sulfonates to said liquid phase soap, wherein the chlorohydroxysulfonates have the formula

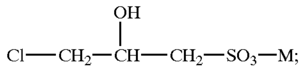

(c) agitating said liquid phase soap with said chlorohydroxy sulfonates to produce a combination liquid phase soap; and (d) drying said combination liquid phase soap in soap manufacturing equipment, wherein the combination soap bar comprises 2 to 35 weight % of monoglyceride sulfonates of the formula

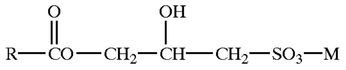

wherein R is an alkyl having 7 to 21 carbon atoms, and M is sodium, potassium, triethanolammonium, or ammonium.

2. The method of claim 1, wherein chlorohydroxy sulfonates comprise 1 to 12 weight % of said combination liquid phase soap.

3. The method of claim 1, wherein chlorohydroxy sulfonates are added to said liquid phase soap in liquid form as a chlorohydroxy sulfonate solution.

4. The method of claim 3, wherein said solution comprises 30 to 45 weight % of chlorohydroxy sulfonate and is manufactured at a temperature ranging from about 40 to 70 degrees centigrade.

5. The method of claim 1 wherein said chlorohydroxy sulfonates are added to said liquid phase soap in solid form as a chlorohydroxy sulfonate powder, wherein the powdered chlorohydroxy sulfonates have over 90 weight % of active constituents.

* * * * *